United States Patent [19]

Krause et al.

[11] Patent Number: 4,867,904
[45] Date of Patent: Sep. 19, 1989

[54] BICYCLOOCTANE DERIVATIVES

[75] Inventors: Joachim Krause, Dieburg; Volker Reiffenrath, Darmstadt, both of Fed. Rep. of Germany; Bernhard Scheuble, Yokohama, Japan; Georg Weber, Erzhausen, Fed. Rep. of Germany

[73] Assignee: Merck Patent Gesellschaft mit Beschrankter Haftung, Darmstadt, Fed. Rep. of Germany

[21] Appl. No.: 46,815

[22] PCT Filed: Aug. 13, 1986

[86] PCT No.: PCT/EP86/00480
§ 371 Date: Apr. 23, 1987
§ 102(e) Date: Apr. 23, 1987

[87] PCT Pub. No.: WO87/01113
PCT Pub. Date: Feb. 26, 1987

[30] Foreign Application Priority Data

Aug. 23, 1985 [DE] Fed. Rep. of Germany ....... 3530126

[51] Int. Cl.$^4$ .................. C09K 19/32; C07C 121/64; C07C 25/22; C07C 43/225
[52] U.S. Cl. ..................... 252/299.62; 252/299.5; 350/350 X; 350/350 S; 558/414; 558/423; 558/425
[58] Field of Search ....... 252/299.61, 299.62, 252/299.63, 295.5; 350/350 R, 350 S; 558/414, 423, 425

[56] References Cited

U.S. PATENT DOCUMENTS

| | | | |
|---|---|---|---|
| 4,219,256 | 8/1980 | Gray et al. | 252/299.62 |
| 4,357,078 | 11/1982 | Carr et al. | 252/299.62 |
| 4,478,740 | 10/1984 | Eidenschime et al. | 252/299.62 |
| 4,490,305 | 12/1984 | Eidenschime et al. | 252/299.63 |
| 4,514,317 | 4/1985 | Huynh-ba et al. | 252/299.62 |
| 4,536,321 | 8/1985 | Sugimori et al. | 252/299.63 |
| 4,551,264 | 11/1985 | Eidenschime et al. | 252/299.62 |
| 4,556,745 | 12/1985 | Carr et al. | 252/299.62 |
| 4,621,901 | 11/1986 | Petrzilka et al. | 252/299.63 |
| 4,659,502 | 4/1987 | Fearon et al. | 252/299.62 |
| 4,664,840 | 5/1987 | Oshan | 252/299.63 |
| 4,707,295 | 11/1987 | Pohl et al. | 252/299.62 |
| 4,710,315 | 12/1987 | Schad et al. | 252/299.63 |
| 4,753,752 | 6/1988 | Raynes et al. | 252/299.62 |
| 4,770,503 | 9/1988 | Buchecker et al. | 252/299.63 |
| 4,797,228 | 1/1989 | Goto et al. | 252/299.63 |

FOREIGN PATENT DOCUMENTS

| | | | |
|---|---|---|---|
| 8188 | 2/1980 | European Pat. Off. | 252/299.62 |
| 84194 | 7/1983 | European Pat. Off. | 252/299.61 |
| 90183 | 10/1983 | European Pat. Off. | 252/299.62 |
| 3500897 | 7/1986 | Fed. Rep. of Germany | 252/299.61 |
| 3510432 | 9/1986 | Fed. Rep. of Germany | 252/299.63 |
| 3606153 | 8/1987 | Fed. Rep. of Germany | 252/299.63 |
| 3606787 | 9/1987 | Fed. Rep. of Germany | 252/299.63 |
| 2081707 | 2/1982 | United Kingdom | 252/299.62 |
| 2121406 | 12/1983 | United Kingdom | 252/299.62 |
| 8603769 | 7/1986 | World Int. Prop. O. | 252/299.61 |

*Primary Examiner*—Teddy S. Gron
*Attorney, Agent, or Firm*—Millen, White & Zelano

[57] ABSTRACT

Bicyclooctane derivatives of the Formula I

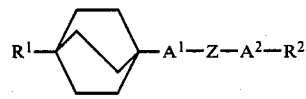

I wherein $R^1$, $R^2$, $A^1$, $A^2$ and Z have the meanings indicated in claim 1, are suitable for use as components of liquid-crystal phases for field effect and/or bistability effect displays.

7 Claims, No Drawings

BICYCLOOCTANE DERIVATIVES

The invention relates to new bicyclooctane derivatives of the Formula I

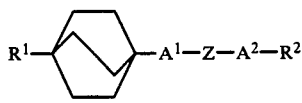

I wherein
$R^1$ and $R^2$ are each an alkyl group which has 1 to 12 C atoms and in which one or two non-adjacent $CH_2$ groups can also be replaced by —O—, —CO—, —O—CO—, —CO—O— and/or —CH=CH—,
$R^1$ is also H and
$R^2$ is also CN,
Z is —CH2CH2—, —CH2O—, —O—CH2— or a single bond
one of the groups $A^1$ and $A^2$ is 1,4-phenylene which is laterally substituted by F or Cl, and the other group is 1,4-phenylene or 1,4-cyclohexylene, and $A^1$ is also a single bond, subject to the provisos that
  (a) one F-substituent in $A^2$ is located in the orthoposition relative to the CN group, if $A^1$ is a single bond, Z is a —CH2CH2— group and $R^2$ is CN,
  (b) $R^2$ is CN, if $A^1$ is a single bond and Z is a —CH2O— group and one F-substituent in $A^2$ is located in the meta-position relative to $R^2$,
  (c) $R^2$ is CN or $R^1$ is H, if $A^1$ is 1,4-cyclohexylene, Z is a single bond and the lateral substituent in $A^2$ is F.

These substances can be used as components of liquid-crystal phases, in particular for displays based on the principle of the twisted cell or the guest-host effect, the field effect or the bi-stability effect.

The invention was based on the problem of finding new, stable, liquid-crystal or mesogenic compounds suitable for use as components of liquid-crystal phases.

It has been found that the bicyclooctane derivatives of the Formula I are excellently suitable for use as components of liquid-crystal phases. In particular, they make it possible to prepare stable liquid-crystal phases which have a relatively high ratio of the elastic constants $K_3/K_1$ and a positive or negative dielectric anisotropy and are particularly suitable for field effect and/or bi-stability effect displays. In field effect displays using mixtures of negative dielectric anisotropy, the phases according to the invention exhibit particularly steep characteristic lines, as a result of which it is possible to achieve high multiplex ratios. In field effect displays using mixtures of positive dielectric anisotropy, the addition of compounds according to the invention results in particularly flat characteristic lines. By this means the number of possible greysteps in TFT-addressed displays based on the principle of the twisted cell or the guest-host effect is decisively enlarged. Compounds of the Formula I wherein $R^2$ is CN are particularly suitable for this purpose.

In liquid-crystal displays having memory properties based on bi-stability effects, the addition of compounds according to the invention results in an increase in tolerance for the uniformity of the layer thickness of the display to the pitch of the liquid-crystal mixture, as a result of which the mass production of such displays is decisively facilitated.

In addition, the provision of the compounds of the Formula I considerably enlarges, in a very general manner, the range of liquid-crystal substances suitable, from various aspects of technical performance in use, for the preparation of liquid-crystal mixtures.

The compounds of the Formula I have a wide field of use.

They can be added to liquid crystal base materials composed of other classes of compounds in order to increase the $K_3/K_1$ values of such a phase, or can themselves serve as a base material having high $K_3/K_1$ values.

The invention therefore relates to the bicyclooctane derivatives of the Formula I and to a process for their preparation which consists in subjecting an appropriate diazonium tetrafluoroborate to thermal decomposition or reacting an appropriate nitro compound with caesium fluoride in order to prepare fluorine compounds, or treating an appropriate diazonium salt with copper (I) chloride in order to prepare chlorine compounds, or treating with a reducing agent a compound which otherwise corresponds to the Formula I but contains one or more reducible group(s) and/or additional C—C bond(s) instead of H atoms, or etherifying an appropriate hydroxyl compound in order to prepare ethers of the Formula I, or reducing a corresponding keto compound in order to prepare compounds of the Formula I containing an ethyl bridge.

The invention also relates to the use of the compounds of the formula I as components of liquid-crystal phases. The invention also relates to liquid-crystal phases containing at least one compound of the Formula I and to liquid-crystal display elements, in particular electrooptical display elements, containing phases of this type.

The radicals $R^1$ and $R^2$ are preferably alkyl having 1–10, in particular 2, 3, 4, 5, 6, 7 or 8, C atoms, and also alkoxy or oxaalkyl having in each case up to 10, preferably 2, 3, 4, 5, 6, 7 or 8, C atoms, and $R^2$ is also preferably CN. They are preferably linear, and are therefore preferably ethyl, propyl, butyl, pentyl, hexyl, heptyl, octyl, and also ethoxy, propoxy, butoxy, pentoxy, heptoxy, octoxy, methoxymethyl, ethoxymethyl, propoxymethyl, butoxymethyl, pentoxymethyl, hexoxymethyl, heptoxymethyl and also methyl, nonyl, decyl, methoxy, nonoxy, decoxy, octoxymethyl, nonoxymethyl and other linear oxaalkyl and dioxaalkyl groups, such as 3-oxabutyl (=2-methoxyethyl), 3-oxapentyl, 4-oxapentyl, 3-, 4- or 5-oxahexyl, 3-, 4-, 5- or 6-oxaheptyl, 3-, 4-, 5-, 6- or 7-oxaoctyl, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl and 1,3- 1,4- 1,5- 2,4- 2,5- or 3,5-dioxahexyl.

Compounds of the Formula I having branched wing groups $R^1$ and/or $R^2$ can occasionally be of importance because of improved solubility in the customary liquid-crystal base materials, but are of particular importance as chiral doping substances, if they are optically active. Branched groups as a rule contain not more than one chain branching.

Preferred branched radicals $R^1$ or $R^2$ are isopropyl, 1-methylpropyl (sec.-butyl) or 2-methylpropyl (isobutyl), 2-methylbutyl, 3-methylbutyl (isopentyl), 2-methylpentyl, 3-methylpentyl, 1-methylhexyl, 2-ethylhexyl, 2-propylpentyl, 1-methylheptyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methoxyhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl or 2-methyl-3-oxahexyl.

Compounds of the Formula I wherein a CH$_2$ group in the radical R$^1$ or R$^2$, preferably in the ω-, ω-1, ω-2, ω-3, ω-4 or ω-5-position, has been a (trans) —CH=CH— group are also preferred.

Compounds of the Formula I wherein R$^1$ is a linear alkyl group having 2 to 8 C atoms and R$^2$ is CN are particularly preferred.

Z in Formula I is preferably a single bond, and also preferably —CH$_2$CH$_2$— or —CH$_2$O—. One of the groups A$^1$ and A$^2$ is a 1,4-phenylene which is laterally substituted by F or Cl, and the other group is preferably 1,4-phenylene and also 1,4-cyclohexylene; A$^1$ is also preferably a single bond.

In the following text, for the sake of simplicity, Bi is the bicyclo(2,2,2)octylene group, Phe is a 1,4-phenylene group, Cy is a 1,4-cyclohexylene group and PheF or PheX is a 1,4-phenylene group which is laterally substituted by X, X being F or Cl. X is preferably fluorine.

The compounds of the Formula I embrace compounds of the partial Formulae Ia to Ib containing two rings:

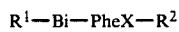  Ia
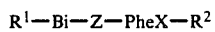  Ib and Ic to Ij containing three rings

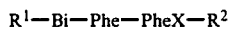  Ic
  Id
  Ie
  If
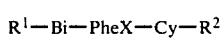  Ig
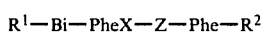  Ih
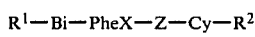  Ii
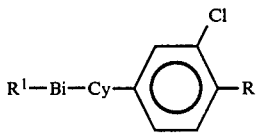  Ij Amongst the above, those of the Formulae Ia, Ib, Ic, Id, If and Ig are particularly preferred.

The compounds of the Formula Ib preferably embrace those of the partial formulae Iba to Ibg:

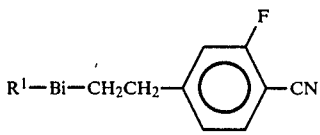  Iba
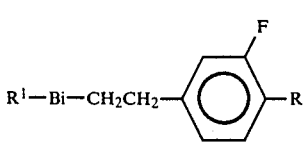  Ibb
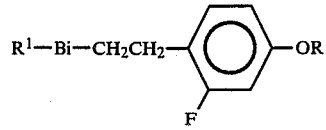  Ibc
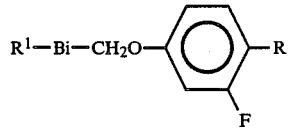  Ibd
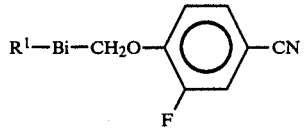  Ibe
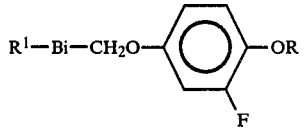  Ibf
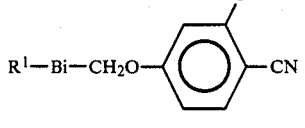  Ibg The compounds of the Formula Id preferably embrace those of the partial formulae Ida to Idf.

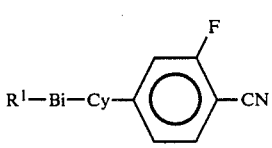  Ida
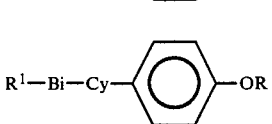  Idb
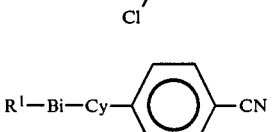  Idc
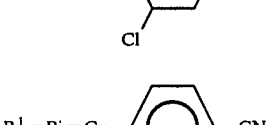  Ide
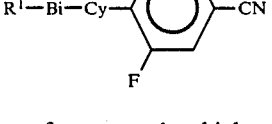  Idf

Groups of compounds which are particularly preferred are those of the formula I of the partial Formulae Ia, Ic and Ig wherein Z is a single bond. In these compounds, the structural element -A¹-A²- is preferably a radical of the Formula (1) to (6),

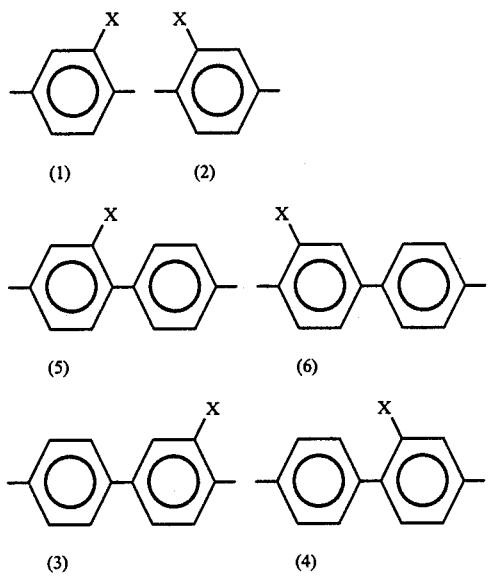

wherein X is fluorine or chlorine. X is preferably fluorine. Radicals of the Formulae (1), (2), (3), (4) and (5) are preferred. Compounds of the Formula I wherein R² is CN and -A¹-A²- is a radical of the Formula (1) or (3) are particularly preferred. Compounds of the Formula I wherein R² is linear alkyl or alkoxy having 2 to 8 C atoms and A¹-A²- is a radical of the formula (2), (4) or (5), preferably (4) or (5), are also preferred.

The preparation of the skeleton of compounds of the Formula I lacking lateral substituents is effected by methods which are known per se and are described in U.S. Pat. No. 4,219,256 and British Patent No. 2,065,104.

The compounds of the Formula I are prepared by methods which are known per se, such as are described in the literature (for example in the standard works such as Houben-Weyl, Methoden der Organischen Chemie ("Methods of Organic Chemistry"), Georg-Thieme-Verlag, Stuttgart), in particular under reaction conditions which are known and suitable for the reactions mentioned. In this regard it is also possible to make use of variants which are known per se but are not mentioned here in detail.

The starting materials can, if desired, also be formed in situ, in a procedure in which they are not isolated from the reaction mixture, but are immediately reacted further to give the compounds of the Formula I.

Thus the compounds of the Formula I can be prepared by reducing a compound which otherwise corresponds to the Formula I, but contains one or more reducible groups and/or C—C bonds instead of H atoms.

Suitable reducible groups are preferably carbonyl groups, in particular keto groups, and also, for example, free or esterified hydroxyl groups or halogen atoms attached to aromatic nuclei. Starting materials which are preferred for the reduction correspond to the Formula I, but can contain a cyclohexene ring or cyclohexanone ring instead of a cyclohexane ring, and/or a —CH=CH— group instead of a —CH₂CH₂— group, and/or a —CO— group instead of a —CH₂— group, and/or a free or functionally modifed (for example in the form of its p-toluenesulfonate) OH group instead of an H atom.

The reduction can, for example, be effected by catalytic hydrogenation at temperatures between about 0° and about 200° and under pressures between about 1 and 200 bar, in an inert solvent, for example an alcohol, such as methanol, ethanol or isopropanol, an ether, such as tetrahydrofuran (THF) or dioxane, an ester, such as ethylacetate, a carboxylic acid, such as acetic acid, or a hydrocarbon, such as cyclohexane. Suitable catalysts are preferably noble metals, such as Pt or Pd, which can be employed in the form of oxides (for example PtO₂ or PdO₂), on a support (for example Pd on charcoal, calcium carbonate or strontium carbonate) or in a finely divided form.

Ketones can also be reduced by the methods of Clemmensen (using zinc, amalgamated zinc or tin and hydrochloric acid, preferably in aqueous-alcoholic solution or in a heterogeneous phase containing water/toluene, at temperatures between about 80 and 120°) or of Wolff-Kishner (using hydrazine, preferably in the presence of an alkali, such as KOH or NaOH, in a high-boiling solvent, such as diethylene glycol or triethylene glycol, at temperatures between about 100 and 200°) to give the corresponding compounds of the Formula I containing alkyl groups and/or —CH₂CH₂— bridges.

Reductions by means of complex hydrides are also possible. For example, it is possible to remove arylsulfonyloxy groups reductively by means of LiAlH₄ and, in particular, to reduce p-toluenesulfonyloxymethyl groups to methyl groups, preferably in an inert solvent, such as diethyl ether or THF, at temperatures between about 0 and 100°. Double bonds can be hydrogenated by means of NaBH₄ or tributyltin hydride in methanol (even in the presence of CN groups!).

Ethers of the Formula I can be obtained by etherifying corresponding hydroxyl compounds, preferably corresponding phenols, the hydroxyl compound being preferably first converted into a corresponding metal derivative, for example converted by treatment with NaH, NaNH₂, NaOH, KOH, Na₂CO₃ or K₂CO₃ into the corresponding alkali metal alcoholate or alkali metal phenolate. The latter can then be reacted with the appropriate alkyl halide or sulfonate or dialkyl sulfate, preferably in an inert solvent, such as acetone, 1,2-dimethoxyethane, DMF or dimethyl sulfoxide, or even in an excess of aqueous or aqueous-alcoholic NaOH or KOH, at temperatures between about 20° and 100°.

Compounds of the Formula I having a —CH₂CH₂— group as a bridge member can, for example, also be prepared by the methods described in German Offenlegungsschrift No. 3,201,721.

The introduction of the fluorine or chlorine atom is also effected by using known methods, such as are described in the literature (for example in the standard works, such as Houben-Weyl, Methoden der Organischen Chemie ("Methods of Organic Chemistry"), Georg-Thieme-Verlag, Stuttgart), in particular under reaction conditions which are known and suitable for the reactions mentioned.

Thus fluorine compounds of the Formula I can be prepared, for example, from the corresponding nitro compounds. These starting materials are obtained by nitrating the skeleton lacking lateral substituents. In this regard, it is possible to influence the distribution of isomers in the resulting mixture of nitration products in the direction of the products principally desired, by suitable choice of the nitration conditions known per se from the literature, for example the nature and concentration of the nitration agent, the solvent, the temperature, the reaction time and/or the catalyst.

These products can then be isolated from the resulting mixtures of isomers in a customary manner, for example by chromatographic processes. The reduction of the nitro compounds to the amino compounds is carried out in accordance with standard methods, for example by catalytic hydrogenation or by treatment with aqueous dithionite or with tin (II) chloride and hydrochloric acid.

Reacting the amino compound with sodium nitrite and tetrafluoroboric acid at −10° to +10° gives the diazonium. tetrafluoroborate, which is then subjected to thermal decomposition at temperatures of 150°–250°, preferably 190°–210°.

A further possible means is the reaction of the corresponding nitro compounds with caesium fluoride in an inert solvent, such as, for example, 1,3-dimethyl-3,4,5,6-tetrahydro-2(1H)-pyrimidone, dimethylformamide or N-methylpyrrolidone, at 80°–150°, preferably 110°–130°.

Chlorine compounds of the Formula I are prepared by converting the corresponding amino compounds in a manner which is known per se (Sandmeyer reaction) into the diazonium salts, and adding copper(I) chloride to the latter and subjecting them to thermal decomposition.

The liquid-crystal phases according to the invention consist of 2 to 20, preferably 3 to 15, components, including at least one compound of the Formula I. The other constituents are preferably selected from nematic or nematogenic substances, particularly the known substances, belonging to the classes comprising azoxybenzenes, benzylideneanilines, biphenyls, terphenyls, phenyl or cyclohexyl benzoates, phenyl or cyclohexyl cyclohexanecarboxyllates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenylpyrimidines, cyclohexylpyrimidines, phenylpyridazines or cyclohexylpyridazines and N-oxides thereof, phenyldioxanes, cyclohexyldioxanes, phenyl-1,3-dithianes, cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolanes and substituted cinnamic acids.

The most important compounds suitable for use as constituents of liquid-crystal phases of this type can be characterized by the Formula I',

R'-L-G-E-R''    I' wherein L and E are each a carbocyclic or ring system belonging to the group composed of 1,4-disubstituted benzene and cyclohexane rings, 4,4'-disubstituted biphenyl, phenylcyclohexane and cyclohexylcyclohexane systems, 2,5-disubstituted pyrimidine rings and 1,3-dioxane rings, 2,6-disubstituted naphthalene, dihydronaphthalene and tetrahydronaphthalene, quinazoline and tetrahydroquinazoline,

| G is | —CH=CH— | —N(O)=N— |
|---|---|---|
| | —CH=CY— | —CH=N(O)— |
| | —C≡C— | —CH₂—CH₂— |
| | —CO—O— | —CH₂—O— |
| | —CO—S— | —CH₂—S— |
| | —CH=N— | —COO—Phe—COO— | or a C—C single bond,

Y is halogen, preferably chlorine, or —CN, and R' and R" are alkyl, alkoxy, alkanoyloxy, alkoxycarbonyl or alkoxycarbonyloxy having up to 18, preferably up to 8, carbon atoms, or one of these radicals is also CN, NC, NO₂, CF₃, F, Cl or Br.

In most of these compounds, R' and R" are different from one another, one of these radicals being in most cases an alkyl or alkoxy group. Other variants of the substituent envisaged are also customary, however. Many of such substances or mixtures thereof are commercially available. All these substances can be obtained in accordance with methods known from the literature.

The phases according to the invention contain about 0.1 to 99, preferably 10 to 95, % of one or more compounds of the Formula I. Liquid-crystal phases according to the invention containing 0.1–40, preferably 0.5–29, % of one or more compounds of the Formula I are also preferred.

Compounds of the Formula I having an optically active wing group are suitable for use as components of nematic liquid-crystal phases for the avoidance of reverse twist and for the improvement of the elastic constants.

These optically active compounds of the Formula I are also suitable for use as components of smectic liquid-crystal phases having a chiral form.

In addition to chiral compounds of the Formula I, these phases contain, in the achiral base mixture, at least one other component having negative dielectric anisotropy or positive dielectric anisotropy small in amount.

Suitable further components having negative dielectric anisotropy are compounds containing the structural element A, B or C:

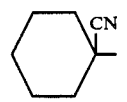   A

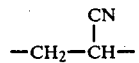   B

   C

Preferred compounds of this type corresponds to the formulae IVa, IV n and IV c:

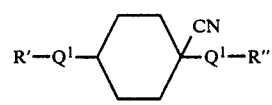   IV a

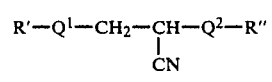   IV b

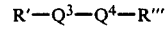   IV c

R' and R" are each preferably linear alkyl or alkoxy groups having 2 to 10 C atoms in each case. Q¹ and Q² are each 1,4-phenylene, trans-1,4-cyclohexylene, 4,4′-biphenylyl, 4-(trans-4-cyclohexyl)-phenyl or trans, trans-4,4′-bicyclohexyl, or one of the groups $Q^1$ and $Q^2$ is also a single bond.

$Q^3$ and $Q^4$ are each 1,4-phenylene, 4,4′-biphenylyl or trans-1,4-cyclohexylene. One of the groups $Q^3$ and $Q^4$ can also be 1,4-phenylene wherein at least one CH groups has been replaced by N. R‴ is an optically active radical containing an asymmetric carbon atom of the structure

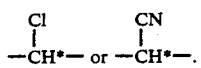

Compounds of the Formula IVc which are particularly preferred are those of the Formula IV c′

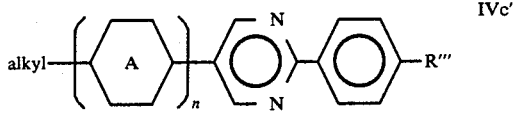

wherein A is 1,4-phenylene or trans-1,4-cyclohexylene and n is 0 or 1.

The preparation of the phases according to the invention is effected in a manner customary per se. As a rule, the components are dissolves in one another, preferably at an elevated temperature.

By means of suitable additives it is possible to modify the liquid-crystal phases according to the invention in such a way that they can be used in all hitherto disclosed types of liquid-crystal display elements and electrooptical display elements.

Additives of this type are known to those skilled in the art and are described in detail in the literature. For example, conducting salts, preferably ethyldimethyldodecylammonium 4-hexyloxybenzoate, tetrabutylammonium tetraphenylboranate, or complex salts of crown ethers (cf., for example, I. Haller et al., Mol. Cryst. Liq. Cryst. Volume 24, pages 249-258 (1973)) can be added in order to improve the conductivity, dichroic dyestuffs can be added in order to prepare coloured guest-host systems, or substances can be added to modify the dielectric anisotropy, the viscosity and/or the orientation of the nematic phases. Substances of this type are described, for example, in German Offenlegungsschrift No. 2,209,127, 2,240,864, 2,321,632, 2,338,281, 2,450,088, 2,637,430, 2,853,728 and 2,902,177.

The following examples are intended to illustrate the invention, without limiting it. In the preceding and following text, percentages are per cent by weight; all temperatures are quoted in degrees centigrade.

EXAMPLE 1

5.64 g of 1-(4-cyano-3-aminophenyl)-4-n-butylbicyclo-[2.2.2]octane (obtainable by reacting the mixture of 2-nitrophenyl and 3-nitrophenyl derivatives obtained in the nitration of 1-(4-bromophenyl)-4-n-butylbicyclo[2.2.2]-octane with copper cyanide in N-methylpyrrolidone, isolating the 1-(4-cyano-3-nitrophenyl)-4-n-butylbicyclo[2.2.2]-octane by chromatography and then reducing it with tin (II) chloride/hydrochloric acid) are dissolved in 25 ml of hot dioxane, and 25 ml of 35 per cent tetrafluoroboric acid are added dropwise, with stirring. After one hour the mixture is cooled to 0°, in the course of which crystallization takes place. A solution of 2.4 g of sodium nitrite in 25 ml of water is added to the suspension, and the mixture is stirred for one hour. The resulting diazonium tetrafluoroborate is filtered off with suction, washed with ice water and dried.

Heating the diazonium salt at 200°, until evolution of gas is complete, gives 1-(4-cyano-3-fluorophenyl)-4-n-butylbicyclo[2.2.2]octane, which is purified by chromatography and crystallization.

The following are prepared analogously:
1-(4-cyano-3-fluorophenyl)bicyclo[2.2.2]octane
1-(4-cyano-3-fluorophenyl)-4-methylbicyclo[2.2.2]octane
1-(4-cyano-3-fluorophenyl)-4-ethylbicyclo[2.2.2]octane
1-(4-cyano-3-fluorophenyl)-4-propylbicyclo[2.2.2]octane
1-(4-cyano-3-fluorophenyl)-4-pentylbicyclo[2.2.2[octane, m.p. 63°, c.p. 53.3°.
1-(4-cyano-3-fluorophenyl)-4-hexylbicyclo[2.2.2]octane
1-(4-cyano-3-fluorophenyl)-4-heptylbicyclo[2.2.2[octane
1-(4-cyano-3-fluorophenyl)-4-octylbicyclo[2.2.2]octane
1-(4-cyano-3-fluorophenyl)-4-nonylbicyclo[2.2.2]octane
1-(4-cyano-3-fluorophenyl)-4-decylbicyclo[2.2.2]octane
1-(4-cyano-3-fluorophenyl)-4-undecylbicyclo[2.2.2]octane
1-(4-cyano-3-fluorophenyl)-4-dodecylbicyclo[2.2.2]octane.

EXAMPLE 2

A diazonium salt solution prepared from 20.1 g of 1-(4-cyano-3-aminophenyl)-4-n-propylbicyclo[2.2.2]octane, 5.2 g of sodium nitrite and 40 ml of 20 per cent hydrochloric acid is added dropwise at 0o to a solution of 9.9 g of Cu(I) chloride in 40 ml of concentrated hydrochloric acid, the mixture is then heated on a boiling water bath until the evolution of gas is complete and is allowed to cool, giving 1-(4-cyano-3-chlorophenyl)-4-n-propylbicyclo[2.2.2]octane by extracting and working up.

The following are prepared analogously:
1-(4-cyano-3-chlorophenyl)bicyclo[2.2.2]octane
1-(4-cyano-3-chlorophenyl)-4-methylbicyclo[2.2.2]octane
1-(4-cyano-3-chlorophenyl)-4-ethylbicyclo[2.2.2]octane
1-(4-cyano-3-chlorophenyl)-4-butylbicyclo[2.2.2]octane
1-(4-cyano-3-chlorophenyl)-4-pentylbicyclo[2.2.2]octane
1-(4-cyano-3-chlorophenyl)-4-hexylbicyclo[2.2.2]octane
1-(4-cyano-3-chlorophenyl)-4-heptylbicyclo[2.2.2]octane
1-(4-cyano-3-chlorophenyl)-4-octylbicyclo[2.2.2]octane
1-(4-cyano-3-chlorophenyl)-4-nonylbicyclo[2.2.2]octane
1-(4-cyano-3-chlorophenyl)-4-decylbicyclo[2.2.2]octane
1-(4-cyano-3-chlorophenyl)-4-undecylbicyclo[2.2.2]octane
1-(4-cyano-3-chlorophenyl)-4-dodecylbicyclo[2.2.2]octane
1-(4′-cyano-3′-chlorobiphenylyl)bicyclo[2.2.2]
1-(4′-cyano-3′-chlorobiphenylyl)-4-methylbicyclo[2.2.2]octane
1-(4′-cyano-3′-chlorobiphenylyl)-4-ethylbicyclo[2.2.2]octane
1-(4′-cyano-3′-chlorobiphenylyl)-4-propylbicyclo[2.2.2]octane 1-(4'-cyano-3'-chlorobiphenylyl)-4-butylbicyclo[2.2.2]octane
1-(4'-cyano-3'-chlorobiphenylyl)-4-pentylbicyclo[2.2.2]octane
1-(4'-cyano-3'-chlorobiphenylyl)-4-hexylbicyclo[2.2.2]octane
1-(4'-cyano-3'-chlorobiphenylyl)-4-heptylbicyclo[2.2.2]octane
1-(4'-cyano-3'-chlorobiphenylyl)-4-octylbicyclo[2.2.2]octane
1-(4'-cyano-3'-chlorobiphenylyl)-4-nonylbicyclo[2.2.2]octane
1-(4'-cyano-3'-chlorobiphenylyl)-4-decylbicyclo[2.2.2]octane
1-(4'-cyano-3'-chlorobiphenylyl)-4-undecylbicyclo[2.2.2]octane
1-(4'-cyano-3'-chlorobiphenylyl)-4-dodecylbicyclo[2.2.2]octane.

EXAMPLE 3

0 85 g of 1-(4-cyano-3-nitrophenyl)-4-n-pentylbicyclo[2.2.2]octane is dissolved in 8 ml of 1,3-dimethyl-3,4,5,6-tetrahydro-2(1H)-pyrimidone, 2.16 g of caesium fluoride are added and the mixture is heated, with stirring, at 120° C. for 2.5 hours. Dilution with water and working up after extraction gives 1-(4-cyano-3-fluorophenyl)-4-n-pentylbicyclo[2.2.2]octane, which is purified by chromatography and crystallization. m.p. 63°; c.p. 53.3°

EXAMPLE 4

The following are prepared analogously to Example 3, starting from the corresponding biphenyl compounds:
1-(4'-cyano-3'-fluorobiphenylyl)bicyclo[2.2.2]octane
1-(4'-cyano-3'-fluorobiphenylyl)-4-methylbicyclo[2.2.2]octane
1-(4'-cyano-3'-fluorobiphenylyl)-4-ethylbicyclo[2.2.2]octane
1-(4'-cyano-3'-fluorobiphenylyl)-4-propylbicyclo[2.2.2]octane
1-(4'-cyano-3'-fluorobiphenylyl)-4-butylbicyclo[2.2.2]octane
1-(4'-cyano-3'-fluorobiphenylyl)-4-hexylbicyclo[2.2.2]octane
1-(4'-cyano-3'-fluorobiphenylyl)-4-heptylbicyclo[2.2.2]octane
1-(4'-cyano-3'-fluorobiphenylyl)-4-octylbicyclo[2.2.2]octane
1-(4'-cyano-3'-fluorobiphenylyl)-4-nonylbicyclo[2.2.2]octane
1-(4'-cyano-3'-fluorobiphenylyl)-4-decylbicyclo[2.2.2]octane
1-(4'-cyano-3'-fluorobiphenylyl)-4-undecylbicyclo[2.2.2]octane
1-(4'-cyano-3'-fluorobiphenylyl)-4-dodecylbicyclo[2.2.2]octane.

EXAMPLE 5:

25 ml of 35 per cent tetrafluoroboric acid are added dropwise, with stirring, to a mixture of 7.5 g of 1-(4'-ethyl with stirring, to a mixture of 7.5 g of 1-(4'-ethyl-2-aminobiphenylyl)-4-n-pentylbicyclo[2.2.2]octane and 25 ml of dioxane. After one hour the mixture is cooled to 0°. A solution of 2.4 g of sodium nitrite in 25 ml of water is added to the suspension, which is stirred for one hour. The resulting diazonium tetrafluoroborate is filtered pff with suction, washed with ice water and dried.

Heating the diazonium salt at 200o until gas evolution is complete gives 1-(4'-ethyl-2-fluorobiphenylyl)-4-n-pentylbicyclo[2.2.2]octane, which is purified by chromatography and crystallization.

The following are prepared analogously:
1-(4'-ethyl-2-fluorobiphenylyl)-4-methylbicyclo[2.2.2]octane
1-(4'-ethyl-2-fluorobiphenylyl)-4-ethylbicyclo[2.2.2]octane
1-(4'-ethyl-2-fluorobiphenylyl)-4-propylbicyclo[2.2.2]octane
1-(4'-ethyl-2-fluorobiphenylyl)-4-butylbicyclo[2.2.2]octane
1-(4'-ethyl-2-fluorobiphenylyl)-4-hexylbicyclo[2.2.2]octane
1-(4'-ethyl-2-fluorobiphenylyl)-4-heptylbicyclo[2.2.2]octane
1-(4'-ethyl-2-fluorobiphenylyl)-4-octylbicyclo[2.2.2]octane
1-(4'-propyl-2-fluorobiphenylyl)-4-methylbicyclo[2.2.2]octane
1-(4'-propyl-2-fluorobiphenylyl)-4-ethylbicyclo[2.2.2]octane
1-(4'-propyl-2-fluorobiphenylyl)-4-propylbicyclo[2.2.2]octane
1-(4'-propyl-2-fluorobiphenylyl)-4-butylbicyclo[2.2.2]octane
1-(4'-propyl-2-fluorobiphenylyl)-4-pentylbicyclo[2.2.2]octane
1-(4'-propyl-2-fluorobiphenylyl)-4-hexylbicyclo[2.2.2]octane
1-(4'-propyl-2-fluorobiphenylyl)-4-heptylbicyclo[2.2.2]octane
1-(4'-propyl-2-fluorobiphenylyl)-4-octylbicyclo[2.2.2]octane
1-(4'-butyl-2-fluorobiphenylyl)-4-methylbicyclo[2.2.2]octane
1-(4'-butyl-2-fluorobiphenylyl)-4-ethylbicyclo[2.2.2]octane
1-(4'-butyl-2'-fluorobiphenylyl)-4-propylbicyclo[2.2.2]octane
1-(4'-butyl-2-fluorobiphenylyl)-4-butylbicyclo[2.2.2]octane
1-(4'-butyl-2-fluorobiphenylyl)-4-pentylbicyclo[2.2.2]octane
1-(4'-pentyl-2-fluorobiphenylyl)-4-ethylbicyclo[2.2.2]octane
1-(4'-pentyl-2-fluorobiphenylyl)-4-propylbicyclo[2.2.2](
1-(4'-pentyl-2'-fluorobiphenylyl)-4-butylbicyclo[2.2.2]octane
1-(4'-pentyl-2-fluorobiphenylyl)-4-pentylbicyclo[2.2.2]octane
1-(4'-methoxy-2-fluorobiphenylyl)-4-methylbicyclo[2.2.2]octane
1-(4'-methoxy-2-fluorobiphenylyl)-4-ethylbicyclo[2.2.2]octane
1-(4'-methoxy-2'-fluorobiphenylyl)-4-propylbicyclo[2.2.2]octane
1-(4'-methoxy-2'-fluorobiphenylyl)-4-butylbicyclo[2.2.2]octane
1-(4'-methoxy-2-fluorobiphenylyl)-4-pentylbicyclo[2.2.2]octane
1-(4'-ethoxy-2-fluorobiphenylyl)-4-methylbicyclo[2.2.2]octane
1-(4'-ethoxy-2-fluorobiphenylyl)-4-ethylbicyclo[2.2.2]octane 1-(4'-ethoxy-2-fluorobiphenylyl)-4-propylbicyclo[2.2.2]octane 1-(4'-ethoxy-2'-fluorobiphenylyl)-4-butylbicyclo[2.2.2]octane 1-(4'-ethoxy-2'-fluorobiphenylyl)-4-pentylbicyclo[2.2.2]octane.

EXAMPLE 6

7.6 g of caesium fluoride are added to a mixture of 3.55 g of 1-[4-pentylbicyclo(2.2.2)octyl]-2-(4-cyano-3-nitrophenyl)ethane (obtainable by nitrating 1-[4-pentylbicyclo(2.2.2)octyl]-2-(4-bromophenyl)-ethane, reacting the product with copper cyanide in N-methylpyrrolidone and subsequently purifying the product by chromatography) and 25 ml of 1,3-dimethyl-3,4,5,6-tetrahydro-2(1H)-pyrimidone, and the mixture is heated at 120oC for 5 hours. Adding water and working up after extraction gives 1-[4-pentylbicyclo(2.2.2)octyl]-2-(4-cyano-3-fluorophenyl)-ethane.

The following are prepared analogously:

1-[4-methylbicyclo(2.2.2)octyl]-2-(4-cyano-3-fluorophenyl)ethane

1-[4-ethylbicyclo(2.2.2)octyl]-2-(4-cyano-3-fluorophenyl)ethane

1-[4-propylbicyclo(2.2.2)octyl]-2-(4-cyano-3-fluorophenyl)ethane

1-[4-butylbicyclo(2.2.2)octyl]-2-(4-cyano-3-fluorophenyl)ethane

1-[4-hexylbicyclo(2.2.2)octyl]-2-(4-cyano-3-fluorophenyl)ethane

1-[4-heptylbicyclo(2.2.2)octyl]-2-(4-cyano-3-fluorophenyl)ethane

1-[4-octylbicyclo(2.2.2)octyl]-2-(4-cyano-3-fluorophenyl)ethane

1-[4-nonylbicyclo(2.2.2)octyl]-2-(4-cyano-3-fluorophenyl)ethane

1-[4-decylbicyclo(2.2.2)octyl]-2-(4-cyano-3-fluorophenyl)ethane

1-[4-undecylbicyclo(2.2.2)octyl]-2-(4-cyano-3-fluorophenyl)-ethane

1-[4-dodecylbicyclo(2.2.2)octyl]-2-(4-cyano-3-fluorophenyl)-ethane.

EXAMPLE 7

1.5 of potassium carbonate are added to a mixture of 3.04 g of 4-pentylbicyclo(2.2.2)octylmethyl methane sulfonate, 1.37 g of 2-fluoro-4-hydroxybenzonitrile and 50 ml of acetone, and the mixture is heated under reflux for 6 hours. The solvent is then removed and the residue is extracted and worked up. Purification by chromatography gives 4-pentylbicyclo(2.2.2)octylmethyl 3-fluorophenyl) ether.

The following are prepared analogously:

4-methylbicyclo(2.2.2)octylmethyl (4-cyano-3-fluorophenyl) ether 4-ethylbicyclo(2.2.2)octylmethyl (4-cyano-3-fluorophenyl) ether 4-propylbicyclo(2.2.2)octylmethyl (4-cyano-3-fluorophenyl) ether 4-butylbicyclo(2.2.2)octylmethyl (4-cyano-3-fluorophenyl) ether 4-hexylbicyclo(2.2.2)octylmethyl (4-cyano-3-fluorophenyl) ether 4-heptylbicyclo(2.2.2)octylmethyl (4-cyano-3-fluorophenyl) ether 4-octylbicyclo(2.2.2)octylmethyl (4-cyano-3-fluorophenyl) ether 4-nonylbicyclo(2.2.2)octylmethyl (4-cyano-3-fluorophenyl) ether 4-decylbicyclo(2.2.2)octylmethyl (4-cyano-3-fluorophenyl) ether 4-undecylbicyclo(2.2.2)octylmethyl (4-cyano-3-fluorophenyl) ether 4-dodecylbicyclo(2.2.2)octylmethyl (4-cyano-3-fluorophenyl) ether The following example of a mixture relates to a liquid-crystal phase according to the invention.

EXAMPLE A

A liquid-crystal phase consisting of:

24% of p-trans-4-propylcyclohexylbenzonitrile,

20% of p-trans-4-butylcyclohexylbenzonitrile,

29% of 1-(4-cyano-3-fluorophenyl)-4-n-pentylbicyclo[2.2.2]octane

5% of 4-butyl-2-cyanophenyl p-trans-4-propylcyclohexylbenzoate and

12% of 4-cyano-4'-(trans-4-pentylcyclohexyl)-biphenyl exhibits the following characteristics:

Clear point: +64° C.

$K_3/K_1$: 2.10.

We claim:

1. A bicyclooctane of the formula I

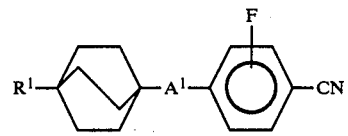

wherein $R^1$ is an alkyl group which has 1 to 12 C atoms and in which one or two non-adjacent $CH_2$ groups can be replaced by —O—, —CO—, —O—CO—, —CO—O— and/or —CH=CH—, and $A^1$ is 1,4-cyclohexylene, 1,4-phenylene or a single bond or of the formula III

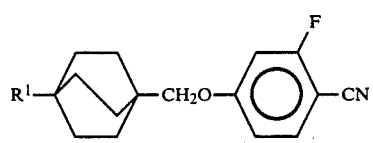

wherein $R^1$ has the meaning given above.

2. A compound of claim 1 of formula I.

3. A compound of claim 1 of formula III.

4. A compound of claim 1 wherein $R^1$ is straight chain alkyl.

5. A liquid-crystal phase containing at least two liquid-crystal components, wherein at least one component is a bicyclooctane derivative of claim 1.

6. A liquid-crystal display element comprising a liquid crystalline phase, wherein said phase is one of claim 5.

7. An electrooptical display element of comprising a liquid crystalline dielectric, wherein the dielectric is a phase of claim 5.

* * * * *